United States Patent
Jou et al.

(10) Patent No.: US 9,803,811 B2
(45) Date of Patent: Oct. 31, 2017

(54) METHOD FOR PRODUCING HIGH-QUALITY LIGHT

(71) Applicant: National Tsing Hua University, Hsinchu (TW)

(72) Inventors: Jwo-Huei Jou, Hsinchu (TW); Zhe-Kai He, Hsinchu (TW)

(73) Assignee: National Tsing Hua University (TW)

( * ) Notice: Subject to any disclaimer, the term of this patent is extended or adjusted under 35 U.S.C. 154(b) by 114 days.

(21) Appl. No.: 15/088,063

(22) Filed: Mar. 31, 2016

(65) Prior Publication Data

US 2017/0211755 A1  Jul. 27, 2017

(30) Foreign Application Priority Data

Jan. 27, 2016  (TW) .............................. 105102520 A

(51) Int. Cl.
  *F21K 9/60* (2016.01)
  *F21V 23/00* (2015.01)
  *F21V 3/00* (2015.01)
  *A61N 5/06* (2006.01)
  *F21Y 115/10* (2016.01)
  *F21Y 115/15* (2016.01)
  *F21Y 113/13* (2016.01)

(52) U.S. Cl.
  CPC .............. *F21K 9/60* (2016.08); *A61N 5/0618* (2013.01); *F21V 3/00* (2013.01); *F21V 23/003* (2013.01); *A61N 2005/0652* (2013.01); *A61N 2005/0653* (2013.01); *A61N 2005/0663* (2013.01); *F21Y 2113/13* (2016.08); *F21Y 2115/10* (2016.08); *F21Y 2115/15* (2016.08)

(58) Field of Classification Search
  CPC .............................. H05B 33/0857; F21K 9/60
  See application file for complete search history.

(56) References Cited

U.S. PATENT DOCUMENTS

| 2009/0184616 | A1* | 7/2009 | Van De Ven | ........ H05B 33/086 313/1 |
| 2010/0177513 | A1* | 7/2010 | Radkov | .............. C09K 11/7734 362/231 |
| 2012/0119658 | A1* | 5/2012 | McDaniel | .......... H05B 33/0857 315/151 |

\* cited by examiner

*Primary Examiner* — Robert May

(57) ABSTRACT

The present invention provides a method for producing high-quality light, wherein this high-quality light producing method consists of a plurality of particularly-designed process steps based on the sensitivity of human eyes and the melatonin suppression. So that, research and development engineers of lighting devices are able to manufacture a high-quality lighting unit or module through this novel method. Moreover, a variety of experimental data have proved that, the high-quality lighting unit produced by using this novel method is able to perform the advantages of high SRI (Spectrum Resemblance Index) and low MLT (Melatonin) suppression rate.

10 Claims, 14 Drawing Sheets

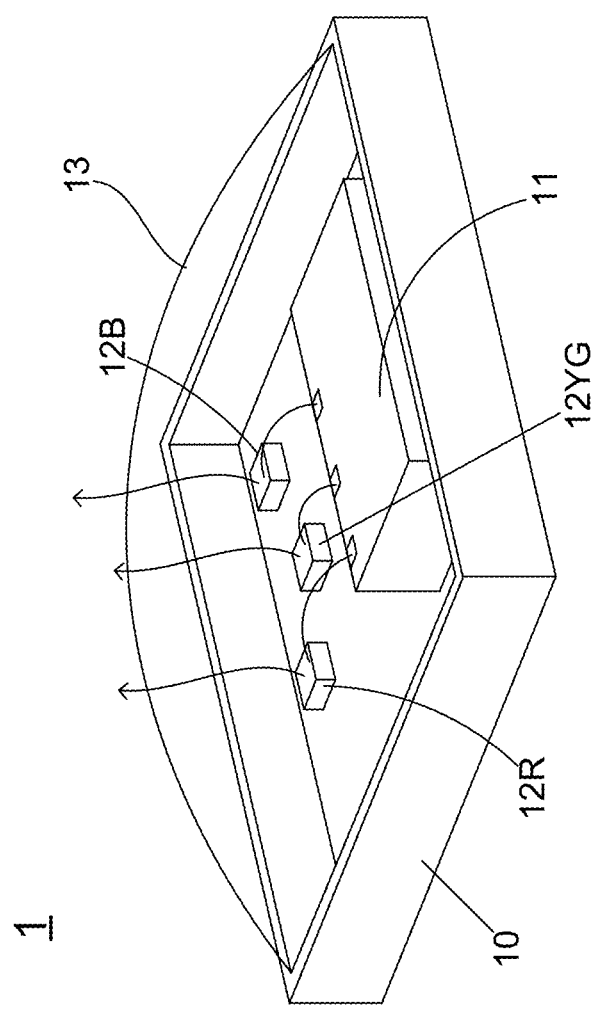

METHOD FOR PRODUCING HIGH-QUALITY LIGHT

BACKGROUND OF THE INVENTION

1. Field of the Invention

The present invention relates to the technology field of high-quality light, and more particularly to a method for producing high-quality light.

2. Description of the Prior Art

Light is an important application in human civilization society. According to natural light emitted by sun, the ancient people are able to rise with the sunrise and take rest with the sunset. With the advancement of the technologies, the artificial light is developed from bulb to incandescent bulb after the Edison invents the bulb. Moreover, the solid-state lighting (SSL), such as light-emitting diode (LED), organic light-emitting diode (OLED) and polymer light-emitting diode (PLED), the latest lighting technology is further be proposed.

ELI (ergonomic lighting indicator) is a comprehensive evaluating standard for lighting quality. Please refer to FIG. 1, there is shown a degree indicator diagram of the ELI. As shown in FIG. 1, ELI includes 5 indicating indices for evaluating a light source, the indicating indices consists of:
(A) visual performance, including the factors of illumination, color rendering, and contrast;
(B) vista, including the factors of user psychology, visual hierarchy, and building materials;
(C) visual comfort, including the factors of light distribution uniformity, the existence of uncomfortable glare, and light flashes;
(D) vitality, including the factors of impacts on people's psychological and stimulation; and
(E) empowerment, including the factors of individual light modulation, selective lighting scenes and layouts.

Therefore, through above descriptions, it is able to know there have 4 indicating indices of the ELI being correspondent with the physiological perception of human, which are visual performance, vista, vitality, and empowerment. Accordingly, it is able to further understand that the human's physiological perception is very important for the ELI.

However, differing from the ELI, CRI (color rendering index) is used for evaluating the light quality by distinct way. The method for measuring the CRI of a light source includes the steps of: Firstly, making a light source to illuminate an object for facilitating the object reveals its object color; next, making a reference light source to illuminate the object for facilitating the object reveals a reference object color. Eventually, quantitatively comparing the object color with the reference object color according to 8 color samples of DIN 6169, therefore the CRI of the light source can be obtained.

Through the method steps for measuring the CRI of the light source, it is able to know that the primary step is comparing the object color with the reference object color according to 8 color samples of DIN 6169; obviously, the CRI-measuring steps does not concern or refer human's physiological perception. Based on this reason, predictably, the light source having high CRI value may not show good ELI values on visual performance, vista, vitality, and empowerment. It means that CRI may not be the best index for light source quality because of lacking fairness and consistency.

On the other hand, researchers have found that the production and the secretion of melatonin are mainly influenced by the following three factors:

(1) Light: light is transmitted to hypothalamus through retinal nerves, and then transmitted to pineal body through the sympathetic nerves, so as to inhibit the secretion of melatonin, therefore the secretion of melatonin can be inhibited in higher level under the darker environment.
(2) Circadian rhythm: hypothalamus, like a biological clock, can affect the secretion of melatonin, so that the concentration of melatonin secreted by pineal body has a significant variation according to circadian rhythm, and the concentration of melatonin in blood in the night is 6 times higher than that in the day according to researches.
(3) Electromagnetic wave: an electromagnetic wave can not only inhibit the ability of pineal body for synthesizing melatonin, but also inhibit the activity of the synthesis of melatonin.

Light is indispensable in daily life. The light perceivable by human eyes is called visible light, wherein the major natural light is sunlight, and the artificial light has various kinds, such as candlelight, incandescent lamps, fluorescent lamps, LED lamp, OLED lamps, etc. Generally speaking, the wavelength range of the visible light is about 450 nm to 750 nm; the color components of the visible light include red, orange, yellow, green, blue, purple, etc.

According to literatures, different color lights would cause different sensitivity to melatonin of human. Please refer to FIG. 2, which shows a diagram of curves representing relativity between light wavelengths and light sensitivity of melatonin. In FIG. 2, curve A represents a photopic luminosity function for the different color lights, and data group shows the light sensitivity caused by the different color lights to melatonin of human. Apparently, in FIG. 2, melatonin has a higher light sensitivity under the color lights having short wavelengths; on the contrary, melatonin has a lower light sensitivity under the color lights having long wavelengths. So that, naturally, for human beings, who are able to avoid melatonin from being suppressed by way of preventing the bodies thereof to be exposed under the light with short wavelength.

Although the data group in the FIG. 2 have proved that melatonin has a higher light sensitivity under the color lights with short wavelengths, literatures have not ever disclosed or recorded the following facts: As shown in FIG. 2, curve B represents melatonin suppression extent per lumen for quanta from different wavelengths. The curve B shows, of course, the quanta from short wavelength light caused higher suppression extent on melatonin under unit lumen; However, to man's surprise, the melatonin suppression extent caused by quanta from long wavelength (around 780 nm) is nearly equal to the melatonin suppression extent caused by quanta from short wavelength (around 480 nm).

According to above descriptions, the most important issue for research and development engineers of lighting products is how to produce a high-quality lighting product simultaneously giving the consideration to the sensitivity of human eyes and the melatonin suppression. In view of that, the inventors of the present application have made great efforts to make inventive research thereon and eventually provided a method for producing high-quality light.

SUMMARY OF THE INVENTION

The primary objective of the present invention is to provide a method for producing high-quality light, wherein this high-quality light producing method consists of a plurality of particularly-designed process steps based on the sensitivity of human eyes and the melatonin suppression. So that, research and development engineers of lighting devices are able to manufacture a high-quality lighting unit or module through this novel method. Moreover, a variety of experimental data have proved that, the high-quality lighting unit produced by using this novel method is able to perform the advantages of high SRI (Spectrum Resemblance Index) and low MLT (Melatonin) suppression rate.

In order to achieve the primary objective of the present invention, the inventor of the present invention provides a method for producing high-quality light, comprising steps of:

(1) providing a plurality of lighting devices, and driving the lighting devices to emit a plurality of color lights;
(2) verifying corresponding CIE coordinates of each of the color lights on a CIE 1931 color space chromaticity diagram, and then determining whether the CIE coordinates of the color lights enclose a Planckian Curve on the CIE 1931 color space chromaticity diagram; if yes, proceeding to step (3); otherwise, proceeding back to the step (1);
(3) mixing the color lights to a mixed light having a specific CIE coordinate on the CIE 1931 color space chromaticity diagram;
(4) determining whether the specific CIE coordinate of the mixed light positions above the Planckian Curve; if yes, proceeding to step (6); otherwise, proceeding to step (5);
(5) driving the plurality of lighting devices to emit the color lights and simultaneously modulating corresponding light intensities of at least one of the color lights, and then proceeding back to the step (3); and
(6) processing or integrating the plurality of lighting devices to a lighting unit or a lighting module, wherein the lighting unit or the lighting module is able to emit a high-quality light.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein:

FIG. 3 shows a stereo diagram of one lighting unit.

DETAILED DESCRIPTION OF THE PREFERRED EMBODIMENTS

To more clearly describe a method for producing high-quality light according to the present invention, embodiments of the present invention will be described in detail with reference to the attached drawings hereinafter.

Figure 1:
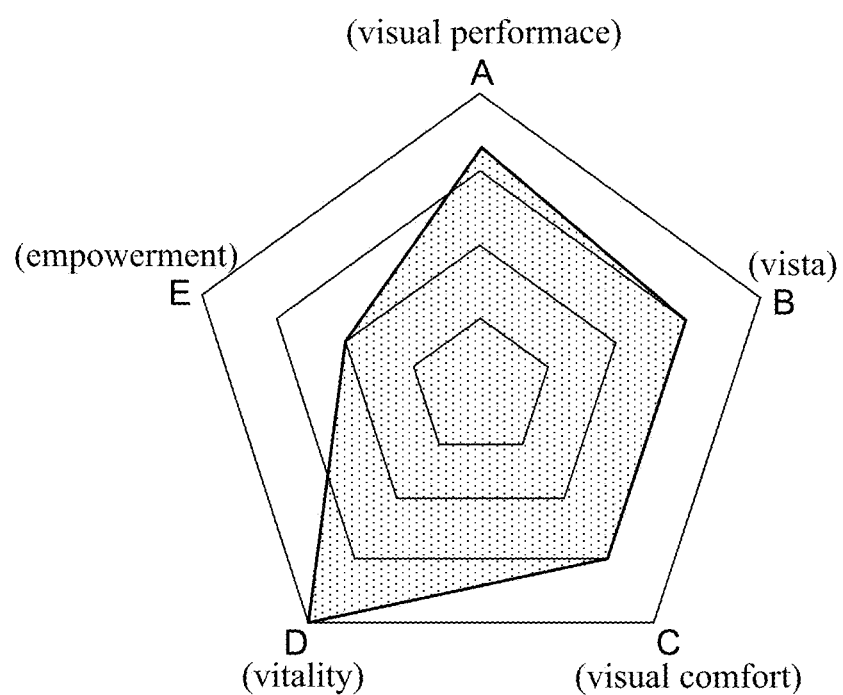
FIG. 1 shows a degree indicator diagram of the ELI.
Figure 2:
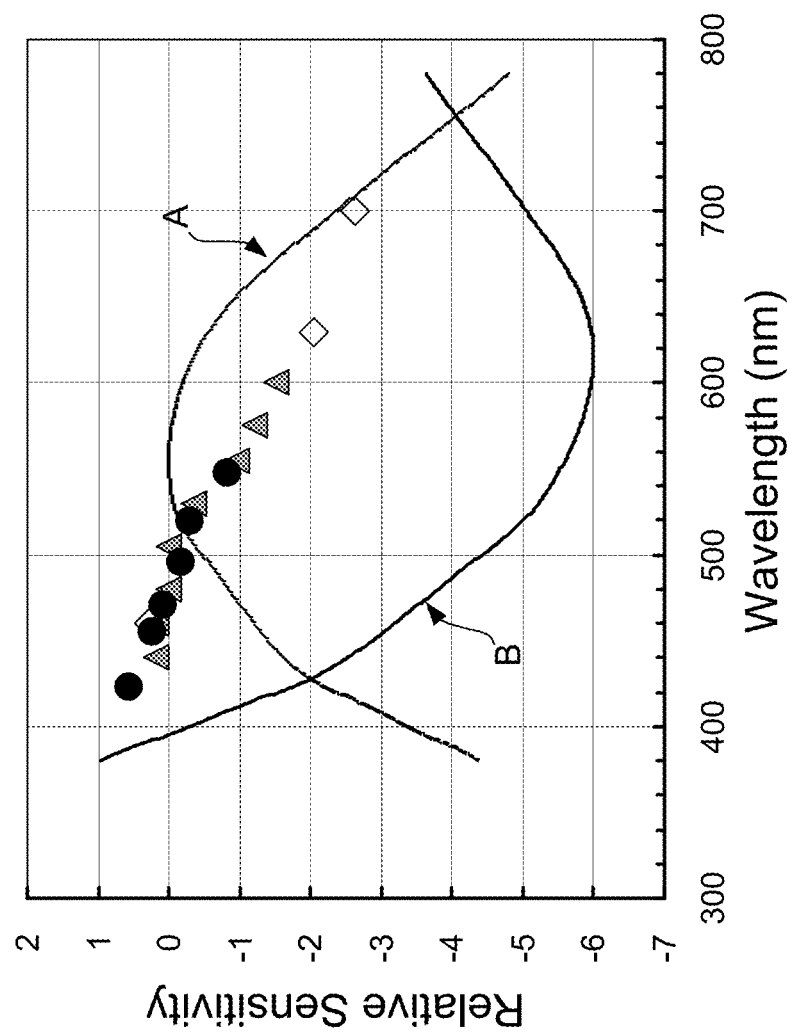
FIG. 2 shows a diagram of curves representing relativity between light wavelengths and light sensitivity of melatonin.

Before starting to introduce the high-quality light producing method of the present invention, it needs to describe a lighting unit (module) consisting of several lighting devices. Please refer to FIG. 3, there is shown a stereo diagram of a lighting unit. The lighting unit 1 consists of: an accommodating body 10, a driving unit 11, three lighting devices, and a transparent cover 13, wherein the lighting device can be an organic light-emitting diode (OLED), an active-matrix organic light-emitting diode (AMOLED) or a light-emitting diode (LED). In FIG. 1, the three lighting devices are respectively a red light chip 12R, a yellow green light chip 12YG and a blue light chip 12B.

Figure 4A:
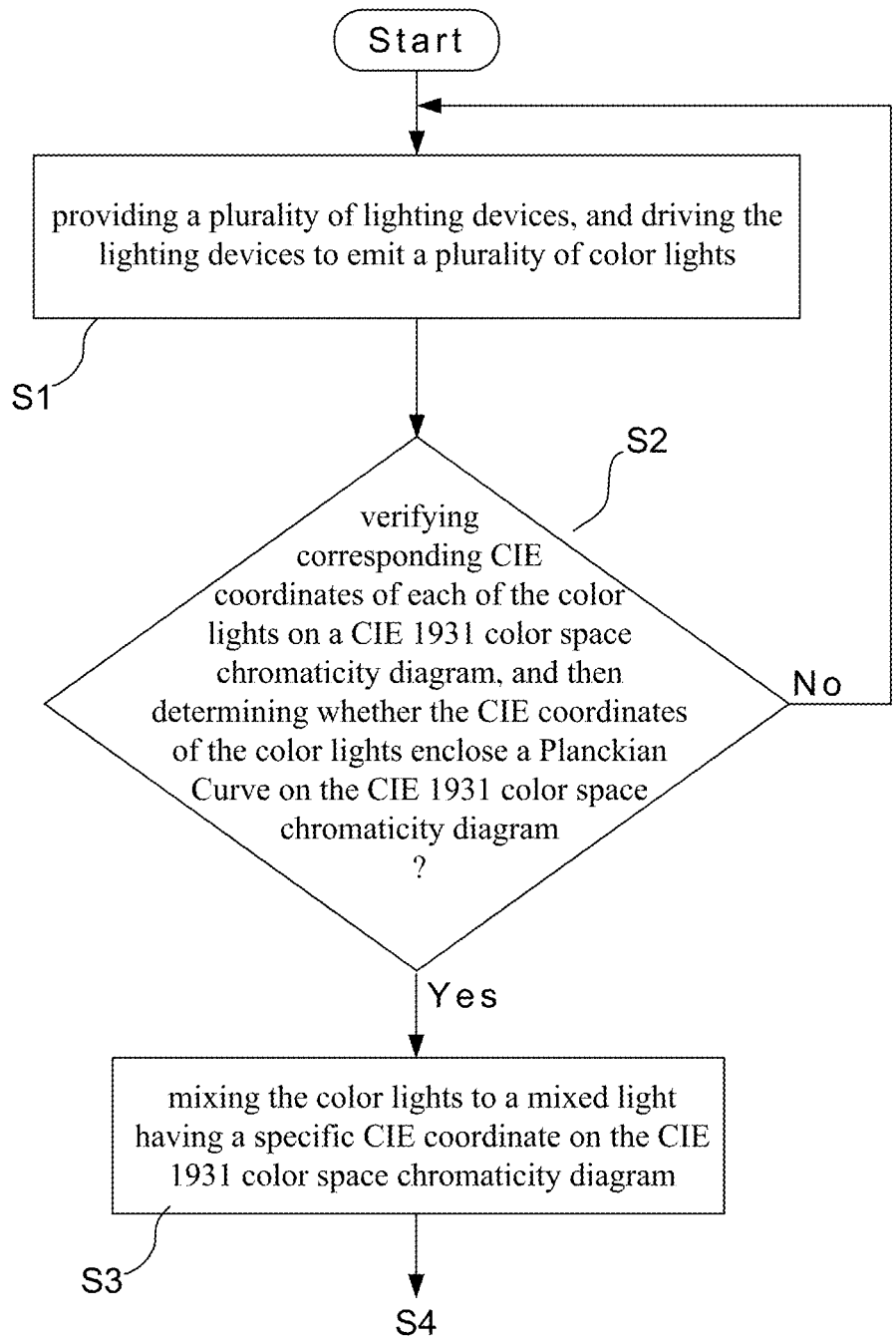
FIG. 4A and FIG. 4B show flowchart diagrams of a method for producing a high-quality light according to the present invention.
Figure 4B:
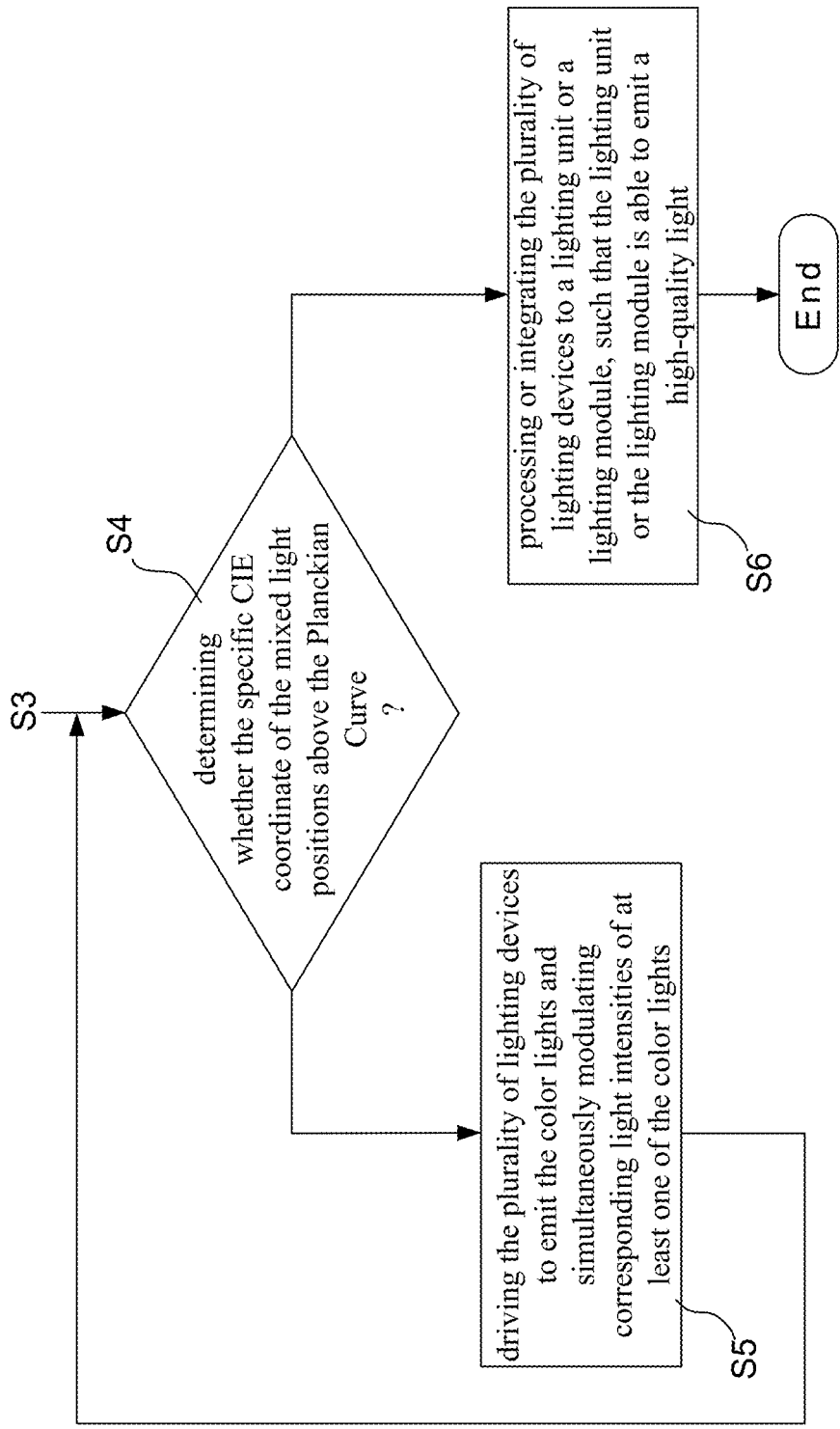

Continuously referring to FIG. 3, and please simultaneously refer to FIG. 4A and FIG. 4B, where flowchart diagrams of the high-quality light producing method provided by the present invention are provided. As FIG. 4A and FIG. 4B show, the method for producing high-quality light mainly comprises 6 processing steps.

Figure 5:
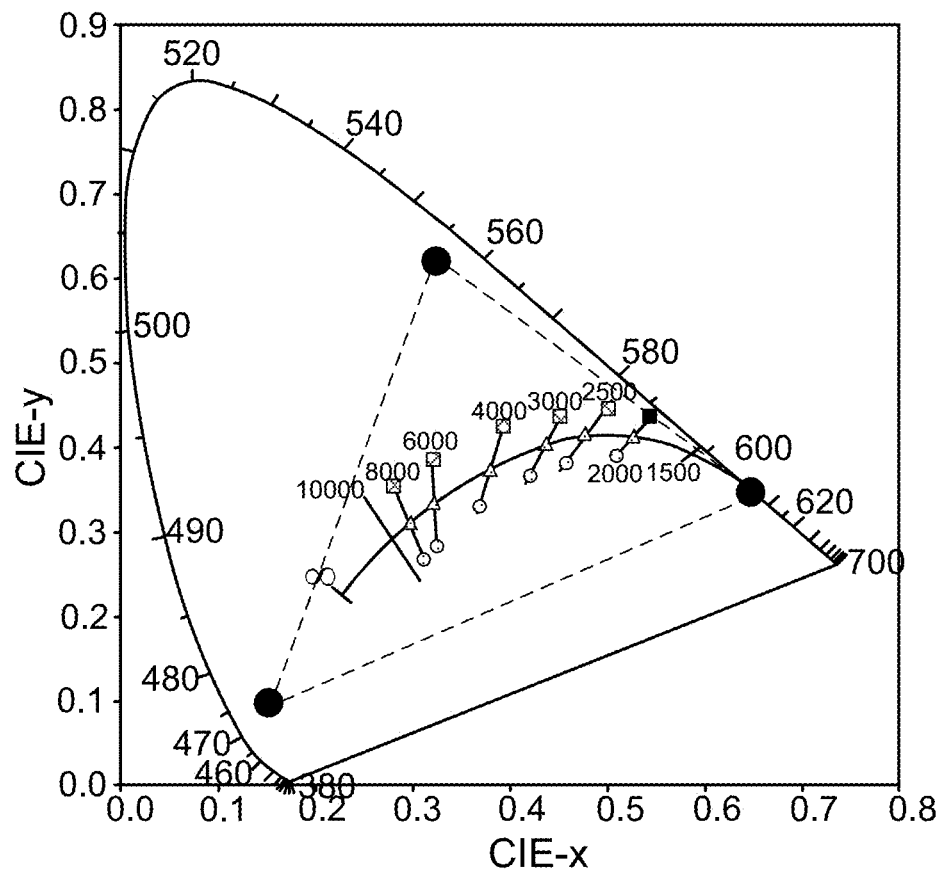
FIG. 5 shows a CIE 1931 color space chromaticity diagram.

Firstly, the method is proceeded to step (S1) for providing a plurality of lighting devices and driving the lighting devices to emit a plurality of color lights. Next, the method is proceeded to step (S2) for verifying corresponding CIE coordinates of each of the color lights on a CIE 1931 color space chromaticity diagram, and then determining whether the CIE coordinates of the color lights enclose a Planckian Curve on the CIE 1931 color space chromaticity diagram. As FIG. 3 shows, the said lighting devices includes a red light chip 12R, a yellow green light chip 12YG and a blue light chip 12B capable of emitting a red light, a yellow green light and a blue light, respectively. Moreover, as the CIE 1931 color space chromaticity diagram provided by FIG. 5 shows, the corresponding CIE coordinates of the red light, the yellow green light and the blue light are respectively (0.64, 0.34), (0.32, 0.62) and (0.15, 0.10). Particularly, a triangular area is enclosed by three lines on the CIE 1931 color space chromaticity diagram for connecting the three CIE coordinates, moreover the Planckian Curve falls in the ranged of the triangular area.

Continuously, the method is proceeded to step (S3) for mixing the color lights to a mixed light having a specific CIE coordinate on the CIE 1931 color space chromaticity diagram. After that, the method is proceeded to step (S4) for determining whether the specific CIE coordinate of the mixed light positions above the Planckian Curve. As FIG. 5 shows, the specific CIE coordinate of the mixed light on the CIE 1931 color space chromaticity diagram is (0.54, 0.43), and the specific CIE coordinate of (0.54, 0.43) positions above the Planckian Curve.

When the determining result of the step (S4) is "No", the method directly proceeds to next step (S5) for driving the plurality of lighting devices to emit the color lights and simultaneously modulating corresponding light intensities of at least one of the color lights. Moreover, after completing the step (S5), the method subsequently proceeds back to the steps (S3)-(S4) in order to verify whether the specific CIE coordinate of the mixed light position above the Planckian Curve or not. On the contrary, when the determining result of the step (S4) is "Yes", the method directly proceeds to next step (S6) for processing or integrating the plurality of lighting devices to a lighting unit or a lighting module, such that the lighting unit or the lighting module is able to emit a high-quality light. That is, as FIG. 3 shows, the light unit 1 integrated with the red light chip 12R, the yellow green light chip 12YG and the blue light chip 12B can emit a high-quality light.

According to a variety of rectangular data points marked on the CIE 1931 color space chromaticity diagram of FIG. 5, it can easily find the CT (color temperature) of the mixed light (i.e., high-quality light) produced through the high-quality light producing method of the present invention is 2000 K. However, that (2000 K) does not used for limit the CT of the high-quality light produced by using present invention's method. According to the instructions and disclosures made by the present invention, it can believes that the engineers skilled in designing and manufacturing lighting units (modules) should be able to produce various high-quality lights with different CT based on their experiences. The corresponding CIE coordinates for the various high-quality lights with different CT are listed in following Table 1.

TABLE 1

| CT (K) | CIE coordinate |
|---|---|
| 2000 | (0.54, 0.43) |
| 3000 | (0.45, 0.43) |
| 4000 | (0.39, 0.42) |
| 5000 | (0.35, 0.38) |
| 6000 | (0.32, 0.37) |
| 7000 | (0.30, 0.35) |
| 8000 | (0.28, 0.34) |

Figure 6:
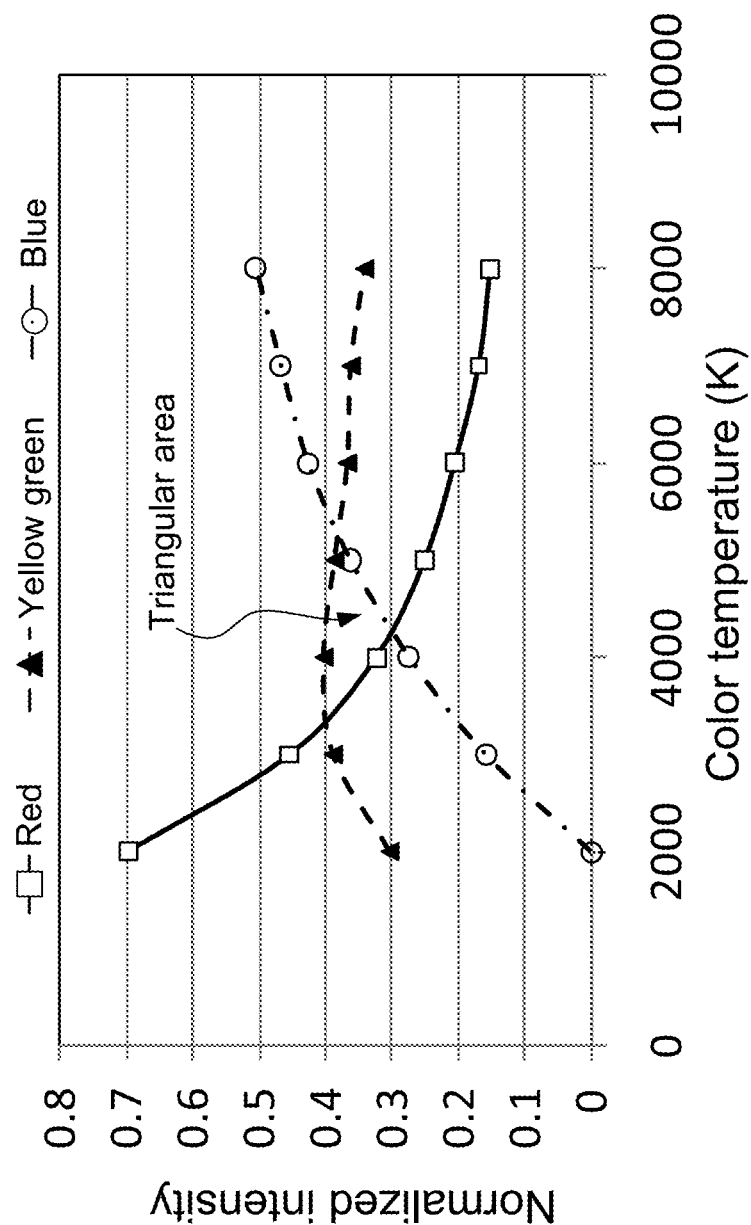
FIG. 6 shows three plot curves of CT versus light intensity.

Please refer to FIG. 6, which illustrates three plot curves of CT versus light intensity. Herein, it needs to further explain that, when executing the step (S5), the red light, the yellow green light and the blue light respectively emitted by the red light chip 12R, the yellow green chip 12YG and the blue light 12B needs to be modulated for respectively showing a plot curve of CT versus red light intensity, a plot curve of CT versus yellow green light intensity and a plot curve of CT versus blue light intensity. Moreover, the plot curve of CT versus red light intensity, the plot curve of CT versus yellow green light intensity and the plot curve of CT versus blue light intensity must intersect to each other for enclosing a triangular area between the aforesaid three plot curves.

So that, based on the three plot curves of CT versus light intensity shown by FIG. 6 and the CIE 1931 color space chromaticity diagram of FIG. 5, it can ensure that each of the corresponding CIE coordinates of various mixed light made of the red light, the yellow green light and the blue light would position above the Planckian Curve, and simultaneously locate at the upper portion of different isotherms on the CIE 1931 color space chromaticity diagram. Therefore, the high-quality light obtained by using the present invention's method would possesses the excellent characteristics of: steady SRI value, low MLT suppression rate, and high theoretical efficiency. The SRI, an abbreviation of spectrum resemblance index, has been proposed and calculated in Taiwan patent No. 1476383 for expressing the light sensitivity of human eyes. On the other hand, calculating method for the MLT suppression rate is disclosed and taught in Taiwan patent No. 1401063.

In following paragraphs, a variety of experimental data are provided for proving the practicability of this high-quality light producing method proposed by the present invention. Following Table 2 has recorded with the data of CRI (color rendering index) and MLT (melatonin) suppression rate of conventional lighting unit.

TABLE 2

| conventional lighting module | CRI | CT (K) | MLT suppression Rate (%) |
|---|---|---|---|
| LED lamp | 81 | 5000 | 56 |
| OLED lamp | 81 | 4800 | 52 |
| cold fluorescent lam | 71 | 5800 | 102 |
| warm fluorescent lam | 82 | 3700 | 71 |

Figure 7A:
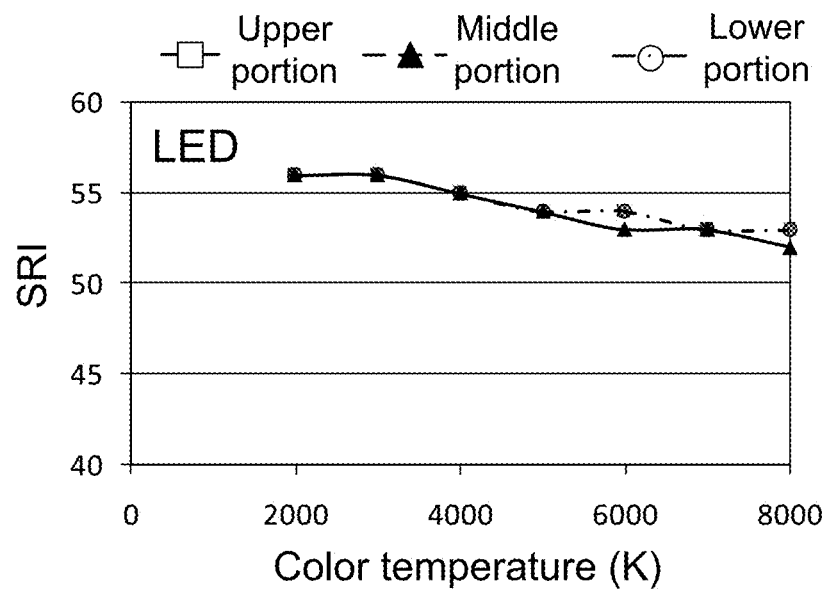
FIG. 7A shows three plot curves of CT versus SRI measured from an LED unit.
Figure 7B:
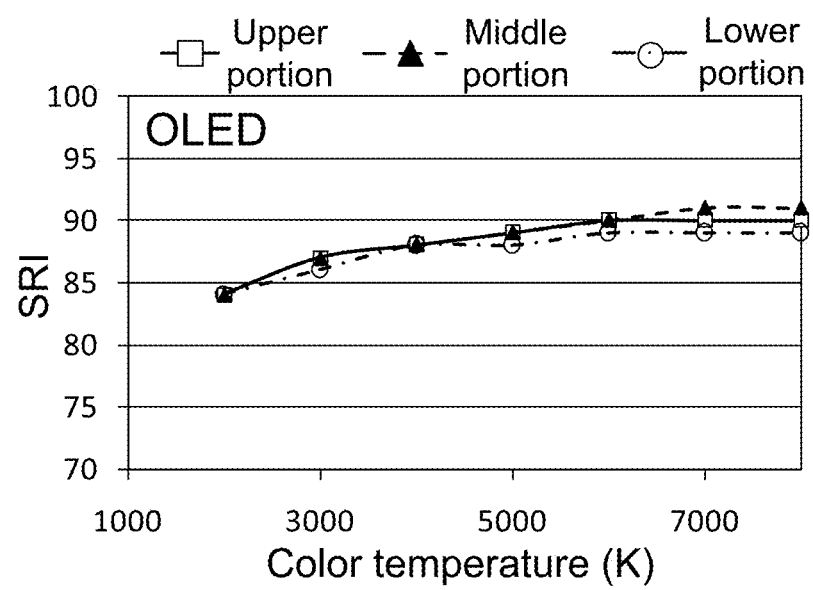
FIG. 7B shows three plot curves of CT versus SRI measured from an OLED unit.

Please refer to FIG. 7A and FIG. 7B, which provide three plot curves of CT versus SRI measured from an LED unit and three plot curves of CT versus SRI measured from an OLED unit. Comparing FIG. 5 with FIG. 7A and FIG. 7B, it is obvious that the rectangular data points marked in FIG. 7A and FIG. 7B are corresponding to the rectangular data points located at the upper portion of the isotherms on the CIE 1931 color space chromaticity diagram of FIG. 5. Moreover, the triangular data points marked in FIG. 7A and FIG. 7B are corresponding to the triangular data points located at the middle portion of the isotherms on the CIE 1931 color space chromaticity diagram of FIG. 5. Furthermore, the circular data points marked in FIG. 7A and FIG. 7B are corresponding to the circular data points located at the lower portion of the isotherms on the CIE 1931 color space chromaticity diagram of FIG. 5. From FIG. 7A and FIG. 7B, it can find that, there have no obvious discrepancies existing between three SRI values measured from three mixed light with different CIE coordinates respectively located at the upper portion, middle portion and lower portion of one identical isotherm.

Figure 8A:
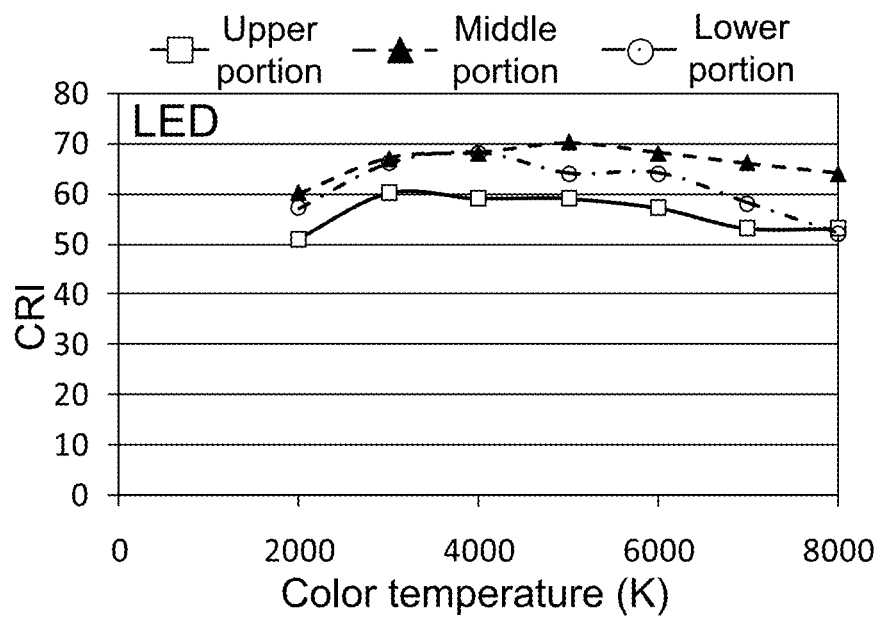
FIG. 8A shows three plot curves of CT versus CRI measured from the LED unit.
Figure 8B:
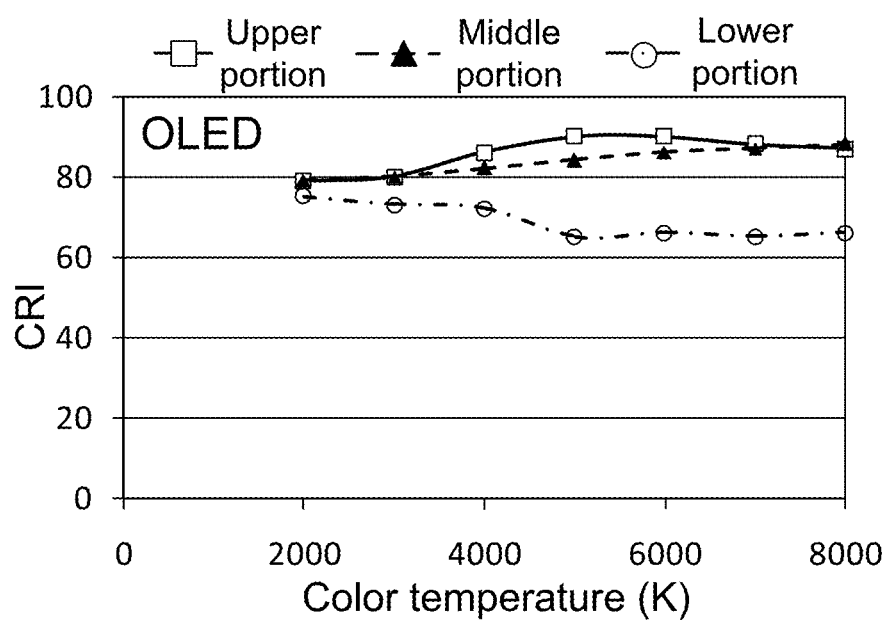
FIG. 8B shows three plot curves of CT versus CRI measured from the OLED unit.

Continuously, please refer to FIG. 8A and FIG. 8B, which provides three plot curves of CT versus CRI measured from the LED unit and three plot curves of CT versus CRI measured from the OLED unit. From FIG. 8A and FIG. 8B, it can find that, the discrepancies between three SRI values measured from three mixed light with different CIE coordinates respectively located at the upper portion, middle portion and lower portion of one identical isotherm are gradually enlarged with the increasing of CT.

Figure 9A:
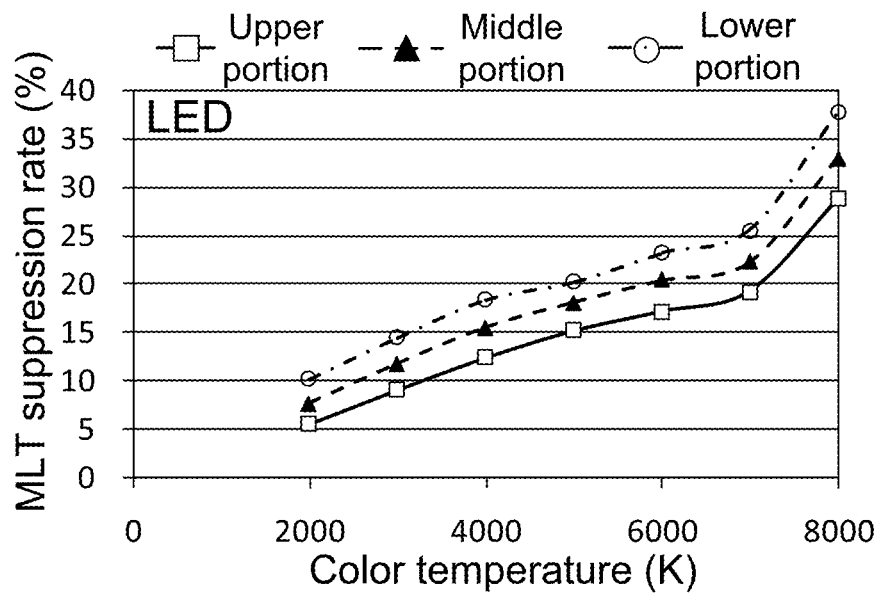
FIG. 9A shows three plot curves of CT versus MLT suppression rate measured from the LED unit.
Figure 9B:
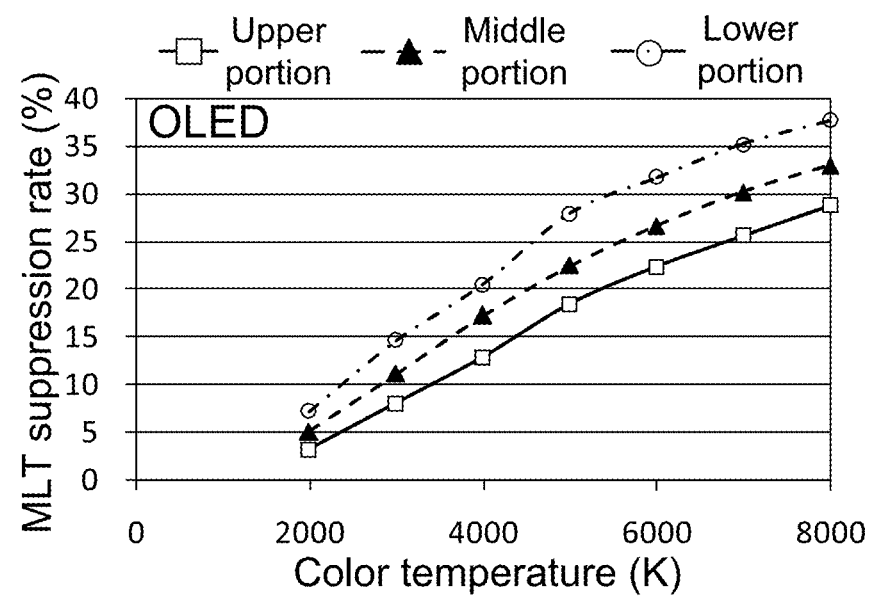
FIG. 9B shows three plot curves of CT versus MLT suppression rate measured from the OLED unit.

Continuously, please refer to FIG. 9A and FIG. 9B, which provides three plot curves of CT versus MLT suppression rate measured from the LED unit and three plot curves of CT versus MLT suppression rate measured from the OLED unit. From FIG. 9A and FIG. 9B, it can find that, the MLT suppression rate measured from three mixed light with different CIE coordinates respectively located at the upper portion, middle portion and lower portion of one identical isotherm gradually increase with the increasing of CT. Notably, the MLT suppression rate measured from the mixed light emitted from the LED lamp and having the CIE coordinate located at the upper portion the isotherm is less than the MLT suppression rate measured from the mixed light emitted from the LED lamp and having the CIE coordinate located at the lower portion the isotherm by 24%. Moreover, the MLT suppression rate measured from the mixed light emitted from the OLED lamp and having the CIE coordinate located at the upper portion the isotherm is less than the MLT suppression rate measured from the mixed light emitted from the OLED lamp and having the CIE coordinate located at the lower portion the isotherm by 34%.

Figure 10A:
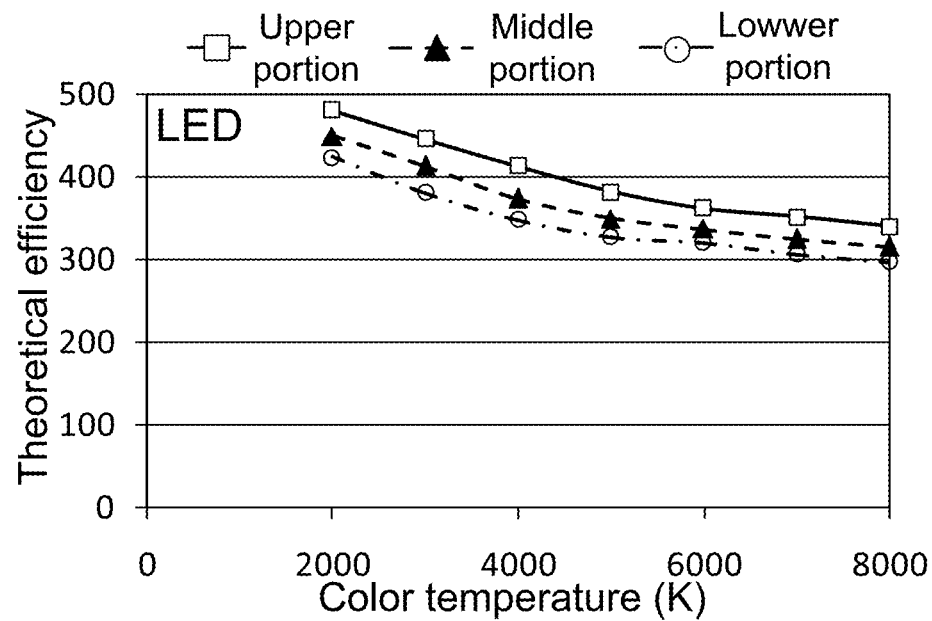
FIG. 10A shows three plot curves of CT versus theoretical efficiency measured from the LED unit.
Figure 10B:
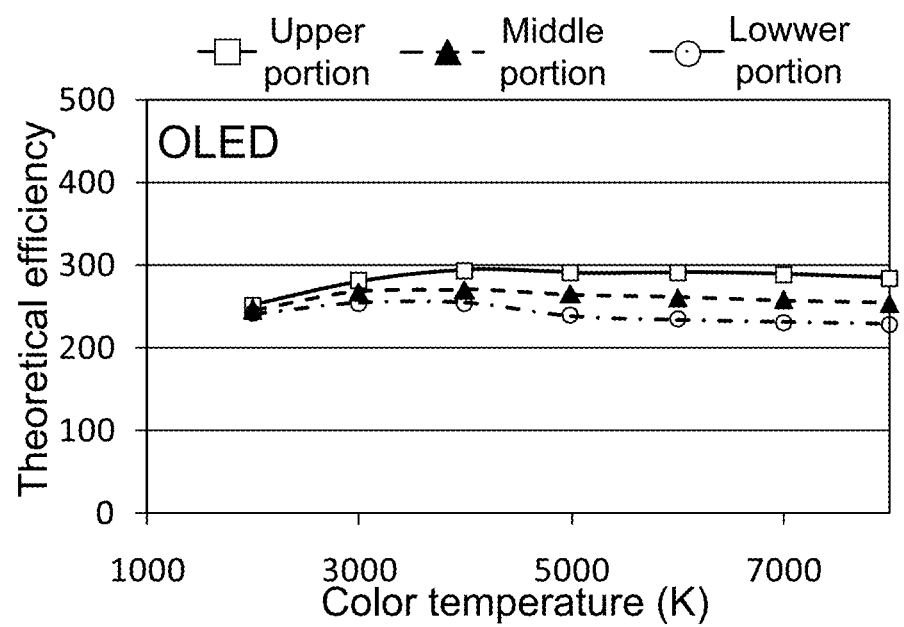
FIG. 10B shows three plot curves of CT versus theoretical efficiency measured from the OLED unit.

Furthermore, please refer to FIG. 10A and FIG. 10B, which provides three plot curves of CT versus theoretical efficiency measured from the LED unit and three plot curves of CT versus theoretical efficiency measured from the OLED unit. From FIG. 10A and FIG. 10B, it can find that, the theoretical efficiency measured from three mixed light emitted from the LED lamp and having different CIE coordinates respectively located at the upper portion, middle portion and lower portion of one identical isotherm gradually decrease with the increasing of CT. Notably, the theoretical efficiency measured from the mixed light emitted from the LED lamp and having the CIE coordinate located at the upper portion the isotherm is higher than the MLF suppression rate measured from the mixed light emitted from the LED lamp and having the CIE coordinate located at the lower portion the isotherm by 16.8%. Moreover, the theoretical efficiency measured from the mixed light emitted from the OLED lamp and having the CIE coordinate located at the upper portion the isotherm is higher than the MLF suppression rate measured from the mixed light emitted from the OLED lamp and having the CIE coordinate located at the lower portion the isotherm by 21.8%.

Therefore, through above descriptions, the method for producing high-quality light provided by the present invention has been introduced completely and clearly; in summary, the present invention includes the advantages of: The present invention particularly provides a method for producing high-quality light, wherein this high-quality light producing method consists of a plurality of particularly-designed process steps based on the sensitivity of human eyes and the melatonin suppression. So that, research and development engineers of lighting devices are able to manufacture a high-quality lighting unit or module through this novel method. Moreover, a variety of experimental data have proved that, the high-quality lighting unit produced by using this novel method is able to perform the advantages of high SRI (Spectrum Resemblance Index) and low MLT (Melatonin) suppression rate.

Figure 11:
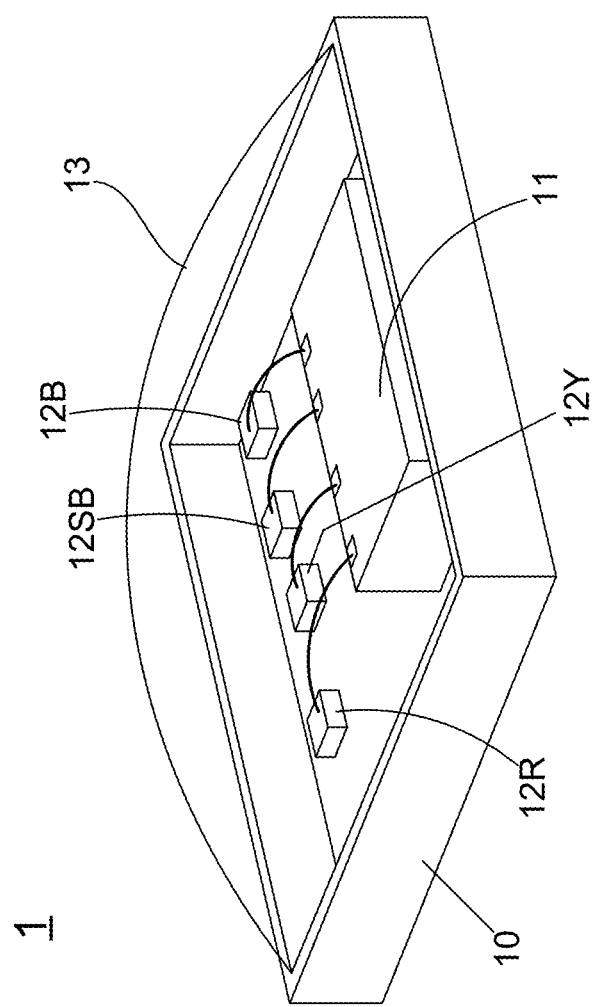
FIG. 11 shows a stereo diagram of another one lighting unit.
Figure 12:
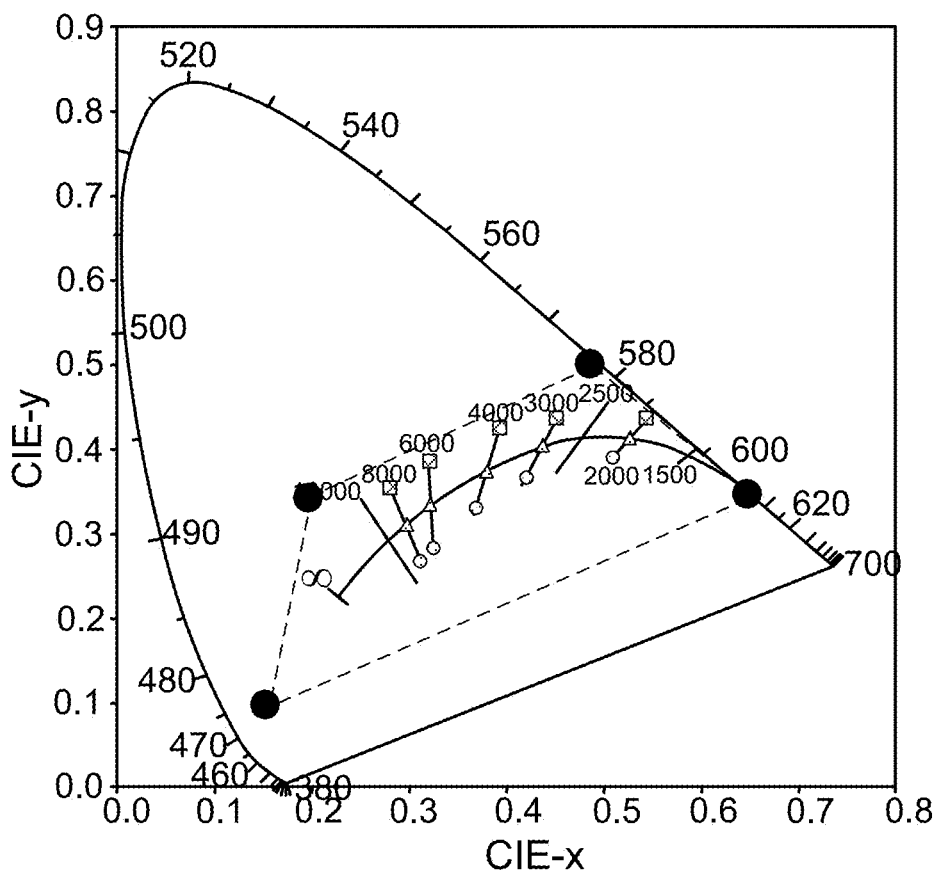
FIG. 12 shows a CIE 1931 color space chromaticity diagram.

Herein, it needs to further explain that, although the experimental data are measured from the lighting unit 1 (module) shown in FIG. 3, that does not used for limiting that the lighting unit 1 can merely consist of three lighting devices (red light chip 12R, yellow green light chip 12YG and blue light chip 12B). In practicable applications, the lighting unit 1 can also consists of four, five or six lighting devices. As the stereo diagram of the lighting unit shown by FIG. 11, the lighting unit 1 comprises: an accommodating body 10, a driving unit 11, four lighting devices, and a transparent cover 13, wherein the lighting devices are a red light chip 12R, a yellow light chip 12Y, a sky blue light chip 12SB, and a blue light chip 12B capable of emitting a red light, a yellow light, a sky blue light, and a blue light, respectively. Moreover, as the CIE 1931 color space chromaticity diagram provided by FIG. 512 shows, the corresponding CIE coordinates of the red light, the yellow light, the sky blue light, and the blue light, are respectively (0.64, 0.34), (0.49, 0.51), (0.18, 0.34), and (0.15, 0.10). Particularly, a quadrangle area is enclosed by three lines on the CIE 1931 color space chromaticity diagram for connecting the three CIE coordinates, wherein the Planckian Curve falls in the ranged of the quadrangle area.

Figure 13:
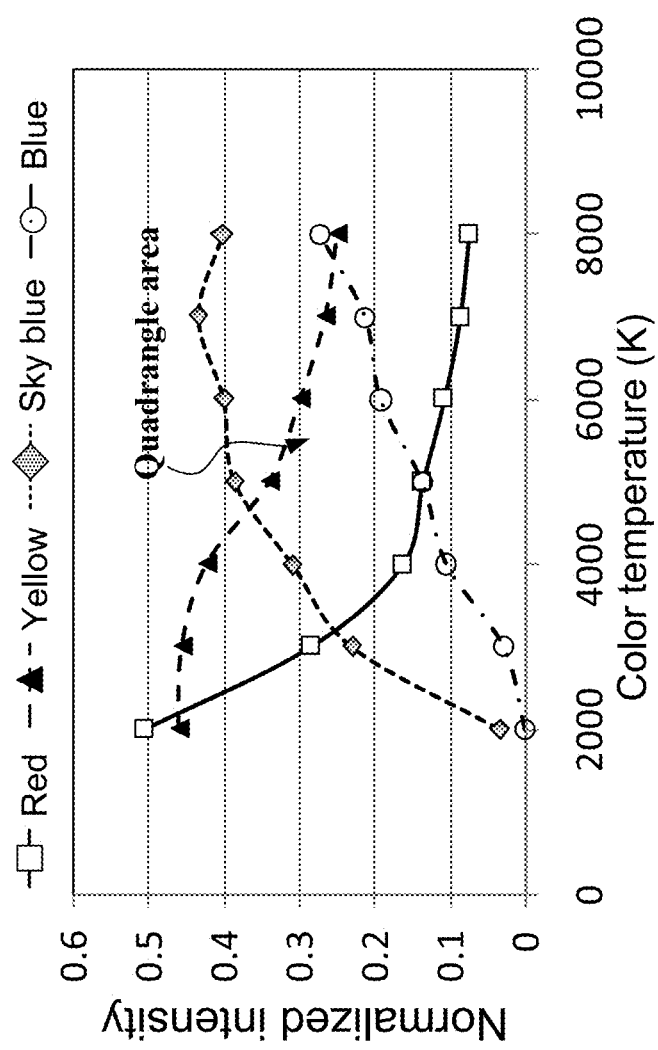
FIG. 13 shows four plot curves of CT versus light intensity.

Please refer to FIG. 13, which illustrates four plot curves of CT versus light intensity. According to flowchart of FIG. 4A and FIG. 4B, the engineer skilled in designing and manufacturing lighting unit (module) has understood that, to producing a high-quality light mixed by the red light, the yellow light, the sky blue light, and the blue light, it needs to modulate the corresponding light intensities of the red light, the yellow light, the sky blue light, and the blue light for respectively showing a plot curve of CT versus red light intensity, a plot curve of CT versus yellow light intensity, a plot curve of CT versus sky blue light intensity, and a plot curve of CT versus blue light intensity. Moreover, the plot curve of CT versus red light intensity, the plot curve of CT versus yellow light intensity, the plot curve of CT versus sky blue light intensity, and the plot curve of CT versus blue light intensity must intersect to each other for enclosing a quadrangle area between the afore said four plot curves.

Similarly, the engineer skilled in designing and manufacturing lighting unit (module) has understood that, to producing a high-quality light mixed by five color lights (i.e., a red light, an orange red light, a yellow light, a green light, and a deep blue light), it needs to modulate the corresponding light intensities of the red light, the orange red light, the yellow light, the green light, and the deep blue light for respectively showing a plot curve of CT versus red light intensity, a plot curve of CT versus orange red light intensity, a plot curve of CT versus yellow light intensity, a plot curve of CT versus green light intensity, and a plot curve of CT versus deep blue light intensity. Moreover, the plot curve of CT versus red light intensity, the plot curve of CT versus orange red light intensity, the plot curve of CT versus yellow light intensity, the plot curve of CT versus green light intensity, and the plot curve of CT versus deep blue light intensity must intersect to each other for enclosing a polygonal area between the aforesaid five plot curves.

Besides, the engineer skilled in designing and manufacturing lighting unit (module) has understood that, to producing a high-quality light mixed by six color lights (i.e., a red light, an orange red light, a yellow light, a green light, a sky blue light, and a deep blue light), it needs to modulate the corresponding light intensities of the red light, the orange red light, the yellow light, the green light, the sky blue light, and the deep blue light for respectively showing a plot curve of CT versus red light intensity, a plot curve of CT versus orange red light intensity, a plot curve of CT versus yellow light intensity, a plot curve of CT versus green light intensity, a plot curve of CT versus sky blue light intensity, and a plot curve of CT versus deep blue light intensity. Moreover, the plot curve of CT versus orange red light intensity, the plot curve of CT versus yellow light intensity, the plot curve of CT versus green light intensity, the plot curve of CT versus sky blue light intensity, and the plot curve of CT versus deep blue light intensity must intersect to each other for enclosing a hexagonal area between the aforesaid six plot curves.

The above description is made on embodiments of the present invention. However, the embodiments are not intended to limit scope of the present invention, and all equivalent implementations or alterations within the spirit of the present invention still fall within the scope of the present invention.

What is claimed is:

1. A method for producing high-quality light, comprising steps of:

(1) providing a plurality of lighting devices, and driving the lighting devices to emit a plurality of color lights;

(2) verifying corresponding CIE coordinates of each of the color lights on a CIE 1931 color space chromaticity diagram, and then determining whether the CIE coordinates of the color lights enclose a Planckian Curve on the CIE 1931 color space chromaticity diagram; if yes, proceeding to step (3); otherwise, proceeding back to the step (1);

(3) mixing the color lights to a mixed light having a specific CIE coordinate on the CIE 1931 color space chromaticity diagram;

(4) determining whether the specific CIE coordinate of the mixed light positions above the Planckian Curve; if yes, proceeding to step (6); otherwise, proceeding to step (5);

(5) driving the plurality of lighting devices to emit the color lights and simultaneously modulating corresponding light intensities of at least one of the color lights, and then proceeding back to the step (3); and (6) processing or integrating the plurality of lighting devices to a lighting unit or a lighting module, wherein the lighting unit or the lighting module is able to emit a high-quality light.

2. The method for producing high-quality light of claim 1, wherein the lighting device is selected from the group consisting of: organic light-emitting diode (OLED), active-matrix organic light-emitting diode (AMOLED) and light-emitting diode (LED).

3. The method for producing high-quality light of claim 1, wherein the color lights comprises: a red light, a yellow green light and a blue light.

4. The method for producing high-quality light of claim 3, wherein the red light, the yellow green light and the blue light are modulated in the step (5), so as to respectively show a plot curve of CT (color temperature) versus red light intensity, a plot curve of CT versus yellow green light intensity and a plot curve of CT versus blue light intensity; moreover, the plot curve of CT (color temperature) versus red light intensity, the plot curve of CT versus yellow green light intensity and the plot curve of CT versus blue light intensity intersect to each other, such that a triangular area is produced between the afore said three plot curves.

5. The method for producing high-quality light of claim 1, wherein the color lights comprises: a red light, a yellow light, a sky blue light, and a deep blue light.

6. The method for producing high-quality light of claim 5, wherein the red light, the yellow light, the sky blue light, and the deep blue light are modulated in the step (5), so as to respectively show a plot curve of CT (color temperature) versus red light intensity, a plot curve of CT versus yellow light intensity, a plot curve of CT versus sky blue light intensity, and a plot curve of CT versus deep blue light intensity; moreover, the plot curve of CT versus red light intensity, the plot curve of CT versus yellow light intensity, the plot curve of CT versus sky blue light intensity, and the plot curve of CT versus deep blue light intensity intersect to each other, such that a quadrangle area is produced between the aforesaid four plot curves.

7. The method for producing high-quality light of claim 1, wherein the color lights comprises: a red light, an orange red light, a yellow light, a green light, and a deep blue light.

8. The method for producing high-quality light of claim 7, wherein the red light, the orange red light, the yellow light, the green light, and the deep blue light are modulated in the step (5), so as to respectively show a plot curve of CT (color temperature) versus red light intensity, a plot curve of CT versus orange red light intensity, a plot curve of CT versus yellow light intensity, a plot curve of CT versus green light intensity, and a plot curve of CT versus deep blue light intensity; moreover, the plot curve of CT (color temperature) versus red light intensity, the plot curve of CT versus orange red light intensity, the plot curve of CT versus yellow light intensity, the plot curve of CT versus green light intensity, and the plot curve of CT versus deep blue light intensity intersect to each other, such that a polygonal area is produced between the aforesaid five plot curves.

9. The method for producing high-quality light of claim 1, wherein the color lights comprises: a red light, an orange red light, a yellow light, a green light, a sky blue light, and a deep blue light.

10. The method for producing high-quality light of claim 9, wherein the red light, the orange red light, the yellow light, the green light, the sky blue light, and the deep blue light are modulated in the step (5), so as to respectively show a plot curve of CT (color temperature) versus red light intensity, a plot curve of CT versus orange red light intensity, a plot curve of CT versus yellow light intensity, a plot curve of CT versus green light intensity, a plot curve of CT versus sky blue light intensity, and a plot curve of CT versus deep blue light intensity; moreover, the plot curve of CT versus orange red light intensity, the plot curve of CT versus yellow light intensity, the plot curve of CT versus green light intensity, the plot curve of CT versus sky blue light intensity, and the plot curve of CT versus deep blue light intensity intersect to each other, such that a hexagonal area is produced between the aforesaid 6 plot curves.

* * * * *